United States Patent [19]

Bracha et al.

[11] Patent Number: 4,551,458
[45] Date of Patent: Nov. 5, 1985

[54] QUINAZOLINES AND FUNGICIDAL COMPOSITIONS THEREOF

[75] Inventors: Peretz Bracha, Omer; Solomon Massil, Beer-Sheva, both of Israel

[73] Assignee: Makhteshim Chemical Works, Ltd., Beer Sheva, Israel

[21] Appl. No.: 483,938

[22] Filed: Apr. 11, 1983

[30] Foreign Application Priority Data

Apr. 11, 1982 [IL] Israel ........................................ 65464

[51] Int. Cl.$^4$ .................... A61K 31/505; C07D 239/80
[52] U.S. Cl. ..................................... 514/259; 544/285
[58] Field of Search ....................... 544/285; 424/251; 514/259

[56] References Cited

U.S. PATENT DOCUMENTS

| 2,553,770 | 5/1951 | Kittleson | 424/274 |
|---|---|---|---|
| 3,544,575 | 12/1970 | Scheuerer et al. | 544/285 |
| 3,681,352 | 8/1972 | Rosenfeld et al. | 544/285 |
| 3,706,748 | 12/1972 | Rosenfeld et al. | 424/251 |
| 3,781,288 | 12/1973 | Rosenfeld et al. | 544/285 |

OTHER PUBLICATIONS

Morrison, et al., *Organic Chemistry*, 2nd Ed., 1966, Allyn & Bacon, Inc., Boston, pp. 740–742, 751–752, 760.
Skinner, G. S. et al., "7-t-Butyl-2,4-Quinanzolinedione", *J. Chem. Soc.*, vol. 77, pp. 5441–5442 (1955).
*Chemical Abstracts*, vol. 66, 104980y (1967).

*Primary Examiner*—Richard L. Raymond
*Assistant Examiner*—James H. Turnipseed
*Attorney, Agent, or Firm*—Browdy and Neimark

[57] ABSTRACT

There are provided novel haloalkylthio-1,3-dihydro 2,4-dioxo-quinazolines having at least one haloalkylthio substituent in the 1- or 3-position; a process for the preparation of such compounds and fungicidal compositions containing same as active ingredient.

13 Claims, No Drawings

QUINAZOLINES AND FUNGICIDAL COMPOSITIONS THEREOF

FIELD OF THE INVENTION

The present invention pertains to new organic chemical compounds, to their method of preparation, to new biocidal compositions, and to a new method of controlling microbes. The present invention is more particularly directed to new 2,4-dioxo-1,3-dihydroquinazolines, to new microbicidal compositions containing the same, and to their use in controlling microbes such as fungi and bacteria.

STATE OF PRIOR ART 2,4-Dioxo-1,3-dihydroquinazolines and their derivatives are known to possess microbicidal and herbicidal activity. For example, Skinner and Zell [J. Am.Chem.Soc.,77(1955)5441] report the synthesis of some 2,4-quinazolinediones and their use as microbicides. U.S. Pat. No. 3,544,575 (C.A.,64:11226a) discloses the preparation of a series of 2,4-quinazolinediones and their use as herbicides. Recently, the pesticidal activity of a variety of 2,4-quinazolinediones was described in U.S. Pat. Nos. 3,681,352; 3,706,748; and 3,781,288. 2-Thiono-4-oxo-1,3-dihydroquinazolines are also known and have been reported by Kappe, et.al [Monatsh. Chem.,98(1967)214(C.A.,66:104980y)] Certain compounds containing >NSCCl$_3$ group, as described in U.S. Pat. No. 2,553,770, are also known to be excellent fungicides.

SUMMARY OF THE INVENTION

We have found a new class of haloalkylthio 1- and 3-substituted 2,4-dioxo- and 2-thiono-4-oxo-1,3-dihydroquinazolines having biocidal activity, particularly against fungi and bacteria. The new haloalkylthio 1- and 3-substituted 2,4-dioxo- and 2-thiono-4-oxo-1,3-dihydroquinazolines can be represented by the following formula:

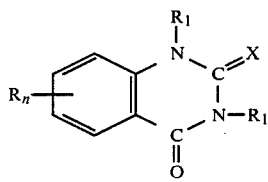

wherein
R is lower alkyl, halogen or nitro,
n is zero or an integer from 1 to 4.
R$_1$ is a haloalkylthio group having 1 or 2 carbon atoms and at least two halogen substituents, lower alkyl, phenyl, halophenyl or halo-lower alkyl phenyl provided that at least one R$_1$ is a haloalkylthio group as defined;
X is oxygen or sulfur.

Examples of R falling within the scope of the present invention are methyl, ethyl, propyl, isopropyl, butyl, pentyl, hexyl, and the respective isomeric forms of these.

Examples of haloalkylthio groups of 1 or 2 carbon atoms (R$_1$) falling wihin the scope of the present invention are bromochlorofluoromethylthio, bromodichloromethylthio, chlorodifluoromethylthio, dichloromethylthio, fluorodichloromethylthio, 1-fluoro-1,1,2,2-tetrachloroethylthio, 1,1,2,2-tetrachloroethylthio, 2,2,2-trichloroethylthio, 1,2,2-trichloroethylthio, trichloromethylthio, and the like. The preferred group is one containing at least three chlorine atoms; and most preferred is the trichloromethylthio group.

The present invention requires that at least one and possibly both R$_1$ groups be haloalkylthio as defined above. A preferred embodiment is when one R$_1$ is a haloalkylthio group and one R$_1$ is an alkyl or aryl hydrocarbon group; and most preferred where one R$_1$ is an alkyl group having from 1 to 4 carbon atoms and X is oxygen.

Specific examples of the 2,4-dioxo-compounds of the present invention are as follows:

1,3-Bis(trichloromethylthio)-2,4-dioxo-1,3-dihydroquinazoline.
1-Trichloromethylthio-3-methyl-2,4-dioxo-1,3-dihydroquinazoline.
1-Trichloromethylthio-3-ethyl-2,4-dioxo-1,3-dihydroquinazoline.
1-Trichloromethylthio-3-n-propyl-2,4-dioxo-1,3-dihydroquinazoline.
1-Trichloromethylthio-3-iso-propyl-2,4-dioxo-1,3-dihydroquinazoline.
1-Trichloromethylthio-3-phenyl-2,4-dioxo-1,3-dihydroquinazoline.
1-Trichloromethylthio-3-p-chlorophenyl-2,4-dioxo-1,3-dihydroquinazoline.
1-Trichloromethylthio-3-m-trifluoromethylphenyl-2,4-dioxo-1,3-dihydroquinazoline.
1,3-Bis(trichloromethylthio)-6-nitro-2,4-dioxo-1,3-dihydroquinazoline.
1-Trichloromethylthio-3-methyl-6-nitro-2,4-dioxo-1,3-dihydroquinazoline.
1-Trichloromethylthio-3-n-propyl-6-nitro-2,4-dioxo-1,3-dihydroquinazoline.
1-Trichloromethylthio-3-iso-propyl-6-nitro-2,4-dioxo-1,3-dihydroquinazoline.
1-Trichloromethylthio-3-phenyl-6-nitro-2,4-dioxo-1,3-dihydroquinazoline.
1,3-Bis(trichloromethylthio)-6-chloro-2,4-dioxo-1,3-dihydroquinazoline.
1,3-Bis(trichloromethylthio)-6-methyl-2,4-dioxo-1,3-dihydroquinazoline.
1,3-Bis(trichloromethylthio)-6-phenyl-2,4-dioxo-1,3-dihydroquinazoline.
1,3-Bis(trichloromethylthio)-6-p-chlorophenyl-2,4-dioxo-1,3-dihydroquinazoline.
1-Methyl-3-trichloromethylthio-2,4-dioxo-1,3-dihydroquinazoline.
1-Phenyl-3-trichloromethylthio-2,4-dioxo-1,3-dihydroquinazoline.
1-p-Chlorophenyl-3-trichloromethylthio-2,4-dioxo-1,3-dihydroquinazoline.
1-m-Trichloromethylphenyl-3-trichloromethylthio-2,4-dioxo-1,3-dihydroquinazoline.
1-Methyl-3-trichloromethylthio-6-nitro-2,4-dioxo-1,3-dihydroquinazoline.
1-Methyl-3-trichloromethylthio-6-chloro-2,4-dioxo-1,3-dihydroquinazoline.
1-Methyl-3-trichloromethylthio-6-methyl-2,4-dioxo-1,3-dihydroquinazoline.
1-3-Bis(bromodichloromethylthio)-2,4-dioxo-1,3-dihydroquinazoline.
1,3-Bis(dichloromethylthio)-2,4-dioxo-1,3-dihydroquinazoline.
1-Dichloromethylthio-3-methyl-2,4-dioxo-1,3-dihydroquinazoline.

1-Dichloromethylthio-3-phenyl-2,4-dioxo-1,3-dihydroquinazoline.
1,3-Bis(1,1,2,2-tetrachloroethylthio)-2,4-dioxo-1,3-dihydroquinazoline.
1-(1,1,2,2,-tetrachloroethylthio)-3-methyl-2,4-dioxo-1,3-dihydroquinazoline.
1,3-Bis(2,2,2-trichloroethylthio)-2,4-dioxo-1,3-dihydroquinazoline.
1-(2,2,2-trichloroethylthio)-3-methyl-2,4-dioxo-1,3-dihydroquinazoline.
1,3-Bis(1,2,2-trichloroethylthio)-2,4-dioxo-1,3-dihydroquinazoline.
1-(1,2,2-trichloroethylthio)-3-methyl-2,4-dioxo-1,3-dihydroquinazoline.

Specific examples of the 2-thiono-4-oxo compounds of the present invention are as follows:
1,3-Bis(trichloromethylthio)-2-thiono-4-oxo-1,3-dihydroquinazoline.
1,3-Bis(trichloromethylthio)-6-nitro-2-thiono-4-oxo-1,3-dihydroquinazoline.
1-Trichloromethylthio-3-methyl-2-thiono-4-oxo-1,3-dihydroquinazoline.
1-Trichloromethylthio-3-n-propyl-2-thiono-4-oxo-1,3-dihydroquinazoline.
1-Trichloromethylthio-3-phenyl-2-thiono-4-oxo-1,3-dihydroquinazoline.
1-Methyl-3-trichloromethylthio-2-thiono-4-oxo-1,3-dihydroquinazoline.
1-Phenyl-3-trichloromethylthio-2-thiono-4-oxo-1,3-dihydroquinazoline.

The new haloalkylthio 2,4-dioxy- and 2-thiono-4-oxo-1,3-dihydroquinazolines of the present invention may be prepared by reacting a haloalkylsulfenyl halide with an alkali metal salt of a 2,4-dioxo- or 2-thiono-4-oxo-1,3-dihydroquinazoline. The reaction is advantageously effected in an aqueous medium, preferably an aqueous solution of an alkali metal hydroxide (e.g., sodium or potassium hydroxide), so as to form the alkali metal salt of the 1,3-disubstituted or 1 or 3-mono-substituted 2,4-dioxo- or 2-thiono-4-oxo-1,3-dihydroquinazolines in-situ. A pre-formed alkali metal salt of the substituted 2,4-dioxo- or 2-thiono-4-oxo-1,3-dihydroquinazolines can also be used if desired. Heat is evolved by the reaction of the alkali metal dioxo- or thiono-oxo-1,3-dihydroquinazolines with the haloalkylsulfenyl halide, so that the reactants should be mixed slowly, accompanied by thorough stirring. The temperature of the reaction mixture is preferably kept at about 0°–5° C., but reaction temperatures as low as about −10° C. and as high as 30° C. can be used. At the higher temperatures the reactants should be mixed slowly. The reaction products separate from the reaction mixture as solids.

The stoichiometry of the reaction requires one or two molecular equivalents of the haloalkylsulfenyl halide for each mole of 2,4-dioxo- or 2-thiono-4-oxo-1,3-dihydroquinazoline depending upon the number of hydrogens being replaced. In either case, however, a slight molar excess of the haloalkylsulfenyl halide is preferred, although an excess of either reactant can be used if so desired.

The new 1-(haloalkylthio)- and 1,3-bis(haloalkylthio)2,4-dioxo and 2-thiono-4-oxo-1,3-dihydroquinazolines are recovered from the reaction mixture and purified by conventional methods. When the desired product is a solid it can be filtered off, washed free of by-products and unreacted starting materials, and recrystallized from a suitable solvent, e.g., ether, petroleum ether, hexane, benzene, pentane, cyclohexane, and the like, or from mixed solvents.

The 2,4-dioxo and 2-thiono-4-oxo-1,3-dihydroquinazoline starting materials can be prepared according to known methods. The 2,4-dioxo-analogues can, illustratively, be prepared by reacting equimolar amounts of aqueous cyanic acid and anthranilic acid and subsequently treating with sodium hydroxide (*Heterocyclic Compounds*, Vol.6, R. C. Elderfield, Editor, John Wiley & Sons, Inc., New York, 1957, pp. 339–341; 584–585). The 2-thiono-analogues can, illustratively, be prepared by fusing isatoic anhydride with thiourea according to the method of Kappe and co-workers mentioned earlier.

The novel haloalkylthio 2,4-dioxo- or 2-thiono-4-oxo-1,3-dihydroquinazolines of the present invention can be formulated as fungicides and bactericides. They can be compounded as standard formulations such as solutions, emulsions, suspensions, powders, pastes and granulates. Those may be produced in known manner, for example by mixing the active compounds with extenders, that is, liquid or solid diluents or carriers, optionally with the use of surface-active agents, that is, emulsifying agents and/or dispersing agents.

As liquid diluents or carriers, there can be used aromatic hydrocarbons, such as xylene or benzene; chlorinated aromatic hydrocarbons such as chlorobenzene; paraffins, such as mineral oil fractions; alcohols such as methanol or butanol; or strongly polar solvents such as dimethylformamide or dimethyl sulphoxide, as well as water.

As solid diluents or carriers, there can be used ground natural minerals, such as kaolins, clays, talc or chalk, or ground synthetic minerals, such as highly-dispersed silicic acid or silicates.

Examples of emulsifying agents include non-ionic and anionic emulsifiers, such as polyoxyethylene-fatty acid esters, polyoxyethylene-fatty alcohol ethers, for example alkylarylpolyglycol ethers, alkyl sulphonates and aryl sulphonates, examples of dispersing agents, include lignin, sulphite waste liquors, and methylcellulose.

The active compounds according to the invention may be present in the formulations in admixture with other active compounds, such as fungicides or other insecticides.

The formulations contain, in general, from 0.1 to 95, preferably 0.5 to 90 percent by weight of active compound.

The active compounds may be used as such or in the form of their formulations prepared therefrom, such as ready-to-use solutions, emulsifiable concentrates, emulsions, suspensions, spray powders, pastes, soluble powders, dusting agents and granulates. Application may take place in the usual manner, for example by watering, squirting, atomizing, vaporization, fumigation, scattering or dusting.

The invention, therefore, provides microbicidal compositions containing as active ingredient a compound according to the invention in admixture with a solid or liquid diluent or carrier.

The invention also provides a method of combating fungi which comprises applying to the pests a composition containing as active ingredient a compound according to the invention in admixture with a solid or liquid diluent or carrier.

EXAMPLE 1

To a suspension of 16.2 g (0.1 mole) 2,4-dioxo-1,3-dihydroquinazoline in 100 ml water was added a solution of 11.2 g (0.2 mole) potassium hydroxide in 25 ml water. To this clear, basic solution was added dropwise a mixture of 37.2 g (0.2 mole) trichloromethanesulfenyl chloride and 1.5 g of an emulsifier (consisting of a mixture of alkyl benzene sulfonate and an ethoxylated castor oil) in 25 ml water while maintaining the reaction mixture at 0°–5° C. The reactants were mixed so that the reaction mixture was kept at a pH greater than 7. The precipitate that formed was filtered off and the filter cake washed with water and air-dried. This was then extracted with hot benzene and the benzene removed under vacuum to yield an oil which solidified on standing. The solid was recrystallized from benzene-cyclohexane to afford 13 g (33%) of 1,3-bis(trichloromethylthio)-2,4-dioxo-1,3-dihydroquinazoline having a melting point of 154°–156° C.

| ANALYSIS (%) | C | H | N | Cl | S |
|---|---|---|---|---|---|
| Calculated ($C_{10}H_4Cl_6N_2O_2S_2$) | 26.04 | 0.87 | 6.07 | 46.20 | 13.88 |
| Found | 26.40 | 0.94 | 5.92 | 45.74 | 14.50 |

Reaction of the benzene insoluble solids with additional trichloromethanesulfenyl chloride followed by the same work-up described above afforded additional product, giving an overall yield of 65%.

EXAMPLE 2

To a suspension of 3.52 g (0.02 mole) 3-methyl-2,4-dioxo-1,3-dihydroquinazoline in 25 ml water was added a solution of 1.12 g (0.02 mole) potassium hydroxide in 15 ml water. To this clear, basic solution was added, dropwise, a mixture of 3.72 g (0.02 mole) trichloromethanesulfenyl chloride and 0.15 g of an emulsifier (as in example 1) in 2.5 ml water while maintaining the reaction mixture at 0°–5° C. The reactants were mixed so that the reaction mixture was kept at a pH greater than 7. The precipitate that formed was filtered off and the filter cake washed with water and air-dried. This was then extracted with hot benzene and the benzene removed under vacuum to yield a semi-solid oil which completely solidified on standing. The solid was recrystallized from benzene-cyclohexane to afford 2.3 g (35%) of 1-trichloromethylthio-3-methyl-2,4-dioxo-1,3-dihydroquinazoline having a melting point of 128°–129° C. Reaction of the benzene insoluble solids with additional trichloromethylsulfenyl chloride followed by the same work-up described above afforded additional product, giving an overall yield of 60%.

EXAMPLE 3

Following the method of Example 1 but using 2.21 g (0.01 mole) 3-methyl-6-nitro-2,4-dioxo-1,3-dihydroquinazoline in 25 ml water, 0.64 g (0.01 mole) potassium hydroxide in 5 ml water, and 1.86 g (0.01 mole) trichloromethanesulfenyl chloride there was obtained after extraction with benzene 2.18 g (58%) of 1-trichloromethylthio-3-methyl-6-nitro-2,4-dioxo-1,3-dihydroquinazoline having a melting point of 170°–171° C.

| ANALYSIS (%) | C | H | N | Cl | S |
|---|---|---|---|---|---|
| Calculated ($C_{10}H_6Cl_3N_3O_4S$) | 32.38 | 1.58 | 11.31 | 28.28 | 8.51 |
| Found | 32.38 | 1.76 | 11.70 | 27.65 | 8.18 |

EXAMPLE 4

Following the method of Example 1 but using 2.04 g (0.01 mole) 3-n-propyl-2,4-dioxo-1,3-dihydroquinazoline in 25 ml water, 0.56 g (0.01 mole) potassium hydroxide, and 1.86 g (0.01 mole) trichloromethanesulfenyl chloride there was obtained 1.64 g (43%) of 1-trichloromethylthio-3-n-propyl-2,4-dioxo-1,3-dihydroquinazoline having a melting point of 120°–121° C.

| ANALYSIS (%) | C | H | N | Cl | S |
|---|---|---|---|---|---|
| Calculated ($C_{12}H_{11}Cl_3N_2O_2S$) | 40.73 | 3.11 | 7.92 | 30.12 | 9.05 |
| Found | 40.68 | 3.25 | 7.32 | 30.50 | 9.13 |

EXAMPLE 5

Following the method of Example 1 but using 2.1 g (0.01 mole) 6-nitro-2,4-dioxo-1,3-dihydroquinazoline in 25 ml water, 0.80 g (0.02 mole) sodium hydroxide, and 3.72 g (0.02 mole) trichloromethylsulfenyl chloride there was obtained 2.35 g (40%) of 1,3-bis(trichloromethylthio)-6-nitro-2,4-dioxo-1,3-dihydroquinazoline having a melting point of 112°–113° C. The NMR spectrum of the compound confirms the structure.

EXAMPLE 6

Following the method of Example 4 but substituting 2.04 g (0.01 mole) 3-iso-propyl-2,4-dioxo-1,3-dihydroquinazoline for the 3-n-propyl-2,4-dioxo-1,3-dihydroquinazoline there was obtained 1.32 g (38%) of 1-trichloromethylthio-3-iso-propyl-2,4-dioxo-1,3-dihydroquinazoline having a melting point of 105°–106° C.

EXAMPLE 7

Following the method of Example 4 but using 2.38 g (0.01 mole) 3-phenyl-2,4-dioxo-1,3-dihydroquinazoline there was obtained 1.28 g (40%) of 1-trichloromethylthio-3-phenyl-2,4-dioxo-1,3-dihydroquinazoline having a melting point of 170°–172° C. The NMR spectrum of the compound confirms the structure.

EXAMPLE 8

Following the method of Example 1 but substituting 1.76 g (0.01 mole) 1-methyl-2,4-dioxo-1,3-dihydroquinazoline for the 3-methyl-2,4-dioxo-1,3-dihydroquinazoline and using 0.40 g (0.01 mole) sodium hydroxide there was obtained 1.2 g (38%) of 1-methyl-3-trichloromethylthio-2,4-dioxo-1,3-dihydroquinazoline having a melting point of 194°–195° C. The NMR spectrum of the compound confirms the structure.

EXAMPLE 9

Following the method of Example 1 but substituting 2.38 g (0.01 mole) 1-phenyl-2,4-dioxo-1,3-dihydroquinazoline for the 3-methyl-2,4-dioxo-1,3-dihydroquinazoline and using 0.40 g (0.01 mole) sodium hydroxide there was obtained 2.25 g (42%) of 1-phenyl-3-trichloromethylthio-2,4-dioxo-1,3-dihydroquinazoline having a melting point of 206°–207° C. The NMR spectrum of the compound confirms the structure.

EXAMPLE 10

Following the method of Example 1 but substituting 3.06 g (0.01 mole) 1-(m-trifluoromethylphenyl)-2,4-dioxo-1,3-dihydroquinazoline for 3-methyl-2,4-dioxo-1,3-dihydroquinazoline and using 0.40 g (0.01 mole) sodium hydroxide there was obtained 1.2 g (30%) of 1-(m-trifluoromethylphenyl)-3-trichloromethylthio-2,4-dioxo-1,3-dihydroquinazoline having a melting point of 179°–180° C. The NMR spectrum of the compound confirms the structure.

| ANALYSIS (%) | C | H | N | Cl | S |
|---|---|---|---|---|---|
| Calculated ($C_{16}H_8Cl_3F_3N_2O_2S$) | 43.46 | 1.85 | 5.73 | 22.32 | 7.20 |
| Found | 42.15 | 1.75 | 6.15 | 23.38 | 7.02 |

Several compounds were tested for their fungicidal activity against *Penicillium chrysogenum* and *Aspergillus niger* using an Agar plate spore germination method based upon that described by M. L. Gattani, Phytopath.,44(1954)113, as follows:

Into a petri dish were placed 8 ml of a malt agar extract and 1 ml of a fungal spore suspension at a constant concentration. The test materials were added to the petri dishes as 1 ml water-acetone solutions at various concentrations containing a small percentage of an emulsifier. Water-acetone solutions containing the same concentrations of emulsifier were used as controls. The results were determined by observing the number of colonies using a colony counter and are expressed in $ED_{50}$ and $ED_{95}$ values.

EXAMPLE 11–15

Compounds were tested against *Aspergillus niger*. The results are listed in Table 1 and compared with Captan as a standard.

EXAMPLES 16–17

Compounds were tested against *Penicillium chrysogenum*. The results are listed in Table 2.

TABLE 1
ACTIVITY AGAINST *ASPERGILLUS NIGER*

| Example | Compound | Formula | $ED_{50}$ (ppm) | $ED_{95}$ (ppm) |
|---|---|---|---|---|
| 11 | 1 | (1-phenyl-3-SCCl₃-2,4-dioxoquinazoline; N—SCCl₃) | 8.0 | 21 |
| 12 | 2 | (N-CH₃ analog, C=O) | 21 | >100 |
| 13 | 3 | (NO₂-substituted, N-CH₃) | 20 | >100 |
| 14 | 4 | (N-(CH₂)₂CH₃ analog) | 2.1 | 15 |
| 15 | 6 | (N-CH(CH₃)₂ analog) | 3.9 | 12 |
| Captan | | (cyclohexene dicarboximide N—SCCl₃) | 0.17 | 3.1 |

TABLE 2
ACTIVITY AGAINST *PENICILLIUM CHRYSOGENUM*

| Example | Compound | Formula | $ED_{50}$ (ppm) | $ED_{95}$ (ppm) |
|---|---|---|---|---|
| 16 | 1 | (N—SCCl₃, SCCl₃) | 8.3 | 13.5 |
| 17 | 2 | (N—CH₃, SCCl₃) | 21 | 91 |

We claim:
1. Compounds having the formula

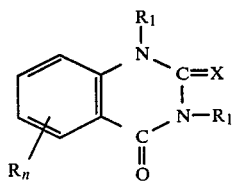

wherein:
R is lower alkyl, halogen or nitro;
R₁ is selected from a haloalkylthio group containing 1 or 2 carbon atoms and at least two halogen substituents; lower alkyl, phenyl, halophenyl, and halo-lower alkyl-phenyl, provided that at least one of R₁ is a haloalkylthio group as defined;
n is zero or an integer of from 1 to 4; and
X is oxygen or sulfur.

2. Compounds according to claim 1, wherein at least one R₁ group is trichloromethylthio.

3. Compounds according to claim 1, wherein X is oxygen.

4. A compound of claim 1, 1,3-bis(trichloromethylthio)-2,4-dioxo-1,3-dihydroquinazoline.

5. A compound of claim 1, 1-trichloromethylthio-3-n-propyl-2,4-dioxo-1,3-dihydroquinazoline.

6. A compound of claim 1, 1-trichloromethylthio-3-iso-propyl-2,4-dioxo-1,3-dihydroquinazoline.

7. A compound of claim 1, 1-(m-trifluoromethylphenyl)-3-trichloromethylthio-2,4-dioxo-1,3-dihydroquinazoline.

8. Fungicidal compositions comprising a solid or liquid diluent or carrier and a fungicidally effective amount of an active compound of the formula

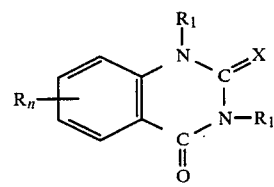

wherein:
R is lower alkyl, halogen or nitro;
R₁ is selected from a haloalkylthio group containing 1 or 2 carbon atoms and at least two halogen substituents; lower alkyl, phenyl, halophenyl, and halo-lower alkyl-phenyl, provided that at least one of R₁ is a haloalkylthio group as defined;
n is zero or an integer of from 1 to 4; and
X is oxygen or sulfur.

9. Compositions according to claim 8, wherein at least one group R₁ is a trichloromethylthio group.

10. Compositions according to claim 8, wherein X is oxygen.

11. A method of controlling fungi which comprises applying to the locus infected with fungi, a fungicidally effective amount of a composition according to claim 8.

12. A fungicidal composition according to claim 8, containing from 0.1 to 95% by weight of the active compound.

13. A fungicidal composition according to claim 8, containing from 0.5 to 90% by weight of the active compound.

* * * * *